United States Patent [19]
Goll et al.

[11] Patent Number: 6,090,046
[45] Date of Patent: Jul. 18, 2000

[54] APPARATUS AND METHOD FOR ULTRASONIC BONE ASSESSMENT

[75] Inventors: Jeffrey H. Goll, Lake Oswego; Hartwell H. Whitney, Portland; Michael Miles, Portland; Maki Myoga, Portland, all of Oreg.

[73] Assignee: Metra Biosystems, Inc., Mountain View, Calif.

[21] Appl. No.: 09/231,467

[22] Filed: Jan. 14, 1999

Related U.S. Application Data

[60] Provisional application No. 60/071,461, Jan. 14, 1998.

[51] Int. Cl.[7] ........................................... A61B 8/00
[52] U.S. Cl. ........................................... 600/438; 600/459
[58] Field of Search .................................. 600/437, 438, 600/459, 460

[56] References Cited

U.S. PATENT DOCUMENTS

| | | | |
|---|---|---|---|
| 5,718,228 | 2/1998 | Hiruta et al. | 600/459 |
| 5,810,732 | 9/1998 | Hamatsu et al. | 600/459 |

FOREIGN PATENT DOCUMENTS

| | | |
|---|---|---|
| 0 747 011 A2 | 12/1996 | European Pat. Off. . |
| 0 761 169 A2 | 3/1997 | European Pat. Off. . |
| WO 90/01296 | 2/1990 | WIPO . |
| WO 93/25146 | 12/1993 | WIPO . |
| WO 96/33657 | 10/1996 | WIPO . |
| WO 96/39080 | 12/1996 | WIPO . |

*Primary Examiner*—Marvin M. Lateef
*Assistant Examiner*—Maulin Patel
*Attorney, Agent, or Firm*—Bromberg & Sunstein LLP

[57] ABSTRACT

An apparatus for performing a measurement that characterizes the behavior of an acoustic wave in a heel bone. The apparatus is an integral unit having a base with a platform coupled to the base at a specified angle with respect to the base for receiving, centering and reproducibly orienting a foot. The apparatus has two transducer arms, each supporting an acoustic transducer in spaced relationship with respect to the foot of the subject and a member for mounting the first and second transducer arms in moveable relationship to the base so as to permit coupled two-dimensional motion of the first and second transducers over regions of the heel. The transducer units have transducer caps and an acoustically absorbing filler medium for emitting an acoustic wave with substantially the character of a point source over an opening angle of at least 30°.

25 Claims, 9 Drawing Sheets

APPARATUS AND METHOD FOR ULTRASONIC BONE ASSESSMENT

The present application claims priority from U.S. provisional application Ser. No. 60/071,461, filed Jan. 14, 1998, which is herein incorporated by reference.

TECHNICAL FIELD

The present invention relates to an apparatus and a method for the acoustic analysis of bone, and more particularly to an apparatus for accomplishing highly reproducible bone measurements using an integral appliance and acoustic transducer elements exhibiting a high degree of insensitivity to the angle at which acoustic energy is propagated into the bone.

BACKGROUND ART

The prior art is rich with approaches to measurement of bone characteristics using acoustic and other methods with a view to identifying patients in need of treatment for osteoporosis. Many acoustic techniques utilize a first transducer to provide an acoustic signal, typically at ultrasonic frequencies, to the subject from a first external location and a second transducer at a second external location disposed on the opposite side of the bone of interest to receive the signal transmitted by the first transducer through the bone and intervening soft tissue. The transducers are often coupled to the subject through a suitable fluid, such as water, or gel. Related techniques are described, for example, in U.S. Pat. No. 5,720,290, issued Feb. 24, 1998, entitled "Apparatus and Method for Acoustic Analysis of Bone Using Optimized Functions of Spectral and Temporal Signal Components," which is hereby incorporated herein by reference. It is known that the derivation of clinically useful data may require highly reproducible measurements across both population samples and from measurement to measurement within an individual.

SUMMARY OF THE INVENTION

The present invention provides, in some embodiments, an apparatus for performing a measurement that characterizes the behavior of an acoustic wave in a bone disposed within the foot of a vertebrate subject. In accordance with a preferred embodiment of the invention, the apparatus has a base having a spatial orientation fixed for a duration of the measurement and a platform for receiving the foot of the subject, the platform being coupled to the base at a specified angle with respect to the base. The apparatus has a foot orientation mechanism for reproducible placement of the foot of the subject on the platform and two transducer arms, each supporting an acoustic transducer in spaced relationship with respect to the foot of the subject. The apparatus also has a member for mounting the first and second transducer arms in moveable relationship to the base so as to permit coupled two-dimensional motion of the first and second transducers over regions of the foot including the calcaneus. Additionally, the apparatus has a waveform generator for causing the first transducer to produce an acoustic waveform that is propagated into the subject and received by the second transducer along a path that includes the bone as well as a processor for determining a characteristic of the behavior of the waveform along the path. The waveform generator, transducer arms and the processor are all contained in an integral assembly.

In accordance with an alternate embodiment of the invention, the orientation mechanism may include a forefoot centering arrangement. The forefoot centering arrangement may include a pair of laterally disposed guides for laterally defining the edges of the foot, the guides being mechanically constrained such that the midpoint between the guides remains fixed regardless of the distance between them.

In accordance with further embodiments of the invention, the apparatus may further include a measuring arrangement for determining the relative displacement of each of the first and second transducer arms for permitting reproducible placement of the foot on the platform, and the measuring arrangement may include sensors for detecting the symmetry of heel placement about a centerline of the platform. Other alternate embodiments of the invention include a heel post for defining the rearward extent of placement of the heel on the platform, a calf positioning mechanism, an Achilles trap for supporting the calf of the subject at a specified orientation with respect to the platform of the apparatus, and a transducer positioning mechanism for varying the spaced relationship of the first and second transducers with the foot of the subject. In particular, the first and second transducer arms may be extensible for permitting the distance between the first transducer and the mounting member and the distance between the second transducer and the mounting member to be varied commensurately. The first and second transducer arms may be coupled to a pivot fixed with respect to the base for permitting motion of each transducer arm in parallel in a direction perpendicular to lines between the pivot and each of the first and second transducers.

In accordance with another aspect of the present invention in one of its embodiments, there is provided a transducer unit for emitting (receiving) an acoustic wave substantially independent of emission (detection) angle for emission (detection) angles less than approximately 30° from a forward direction. The transducer unit has a piezo-electric element having a lateral dimension and an axial dimension for generating the acoustic wave. The piezo-electric element is surrounded circumferentially and in the forward direction by a transducer cap having a wall with an interior surface intimately coupled to the piezo-electric element in a contact region in no more than the forward direction. The transducer unit also has a backing for absorbing acoustic energy radiated by the piezo-electric element in a posterior direction and a damping material for filling a volume lateral to and posterior to the piezo-electric element and the backing In accordance with another embodiment of the invention, the inner surface of the wall of the transducer cap outside the contact region may be angled in such a manner as to reflect acoustic energy impinging upon it away from the piezo-electric element. The lateral dimension of the piezo-electric element may be less than twice the axial dimension of the piezo-electric element and the transducer cap may extend beyond the piezo-electric element in the forward direction for a distance selected such that the transient response is optimized and variations of the acoustic output with respect to temperature and angle are minimized. The transducer cap may include plastic and the damping filler may include polyurethane. The polyurethane may be formulated to absorb ultrasound. A forward portion of the wall of the transducer cap may be curved so as to tailor conversion between longitudinal modes of acoustic energy and shear modes of acoustic energy for favorable combination of the modes to acoustic energy propagated in the subject. More particularly, the forward portion of the wall of the transducer cap may have a shape of hemispherical section.

In accordance with yet another aspect of the present invention, there is provided a method for characterizing the behavior of an acoustic wave in a bone disposed within a foot of a vertebrate subject. The method has the steps of:

a. providing an apparatus having:
  i. a platform for receiving the foot of the subject;
  ii. a first transducer arm for supporting a first acoustic transducer in spaced relationship with respect to the foot of the subject;
  iii. a second transducer arm for supporting a second acoustic transducer in spaced relationship with respect to the foot of the subject;
  iv. a member for mounting the first and second transducer arms in moveable relationship to the base so as to permit coupled two-dimensional motion of the first and second transducers over regions of the foot including the calcaneus; and
  v. a processor for determining a characteristic of the behavior of the waveform along the path; a
wherein the waveform generator, the transducer arms, and the processor are contained in an integral assembly;
b. orienting the foot of the subject in a specified and reproducible orientation with respect to the platform;
c. exciting an acoustic wave for propagation into the subject with the first transducer;
d. receiving the acoustic wave with the second transducer; and
e. calculating a characteristic of the waveform along the path.

BRIEF DESCRIPTION OF THE DRAWINGS

The foregoing features of the present invention will be more readily understood by reference to the following detailed description taken with the accompanying drawings, in which.

DETAILED DESCRIPTION OF SPECIFIC EMBODIMENTS

Figure 1:
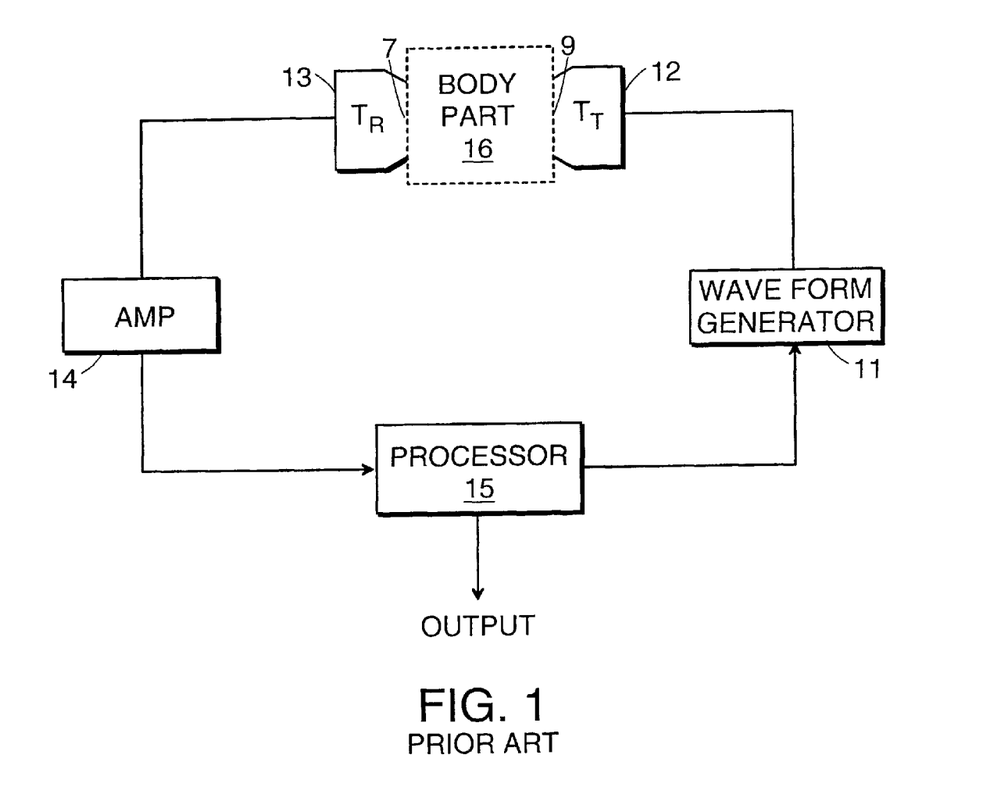
FIG. 1 is a diagram showing in general the components for an ultrasound diagnostic system as known in the prior art, having coaxial transducer axes and flat transducer faces.

FIG. 1 is a diagram showing in general the components of a prior art acoustic measurement system. In this system, a waveform is generated by waveform generator 11, and delivered to transmitting transducer $T_T$, item 12. The transducer $T_T$ is acoustically coupled to body part 16 of a subject and produces an acoustic wave that is propagated into the body part 16 and in particular into a bone within the body part. The transducer $T_R$, item 13, is also acoustically coupled to the body part 16 and receives a signal resulting from the effects, among other things, of propagation of the acoustic wave through the bone and the body part. The longitudinal axes of transducers $T_T$ and $T_R$ are coaxially aligned, and faces 7 and 9 of transducers $T_T$ and $T_R$ are flat and substantially parallel. The output of the transducer $T_R$ is amplified by amplifier 14 and processed by processor 15. The processor analyzes the output of the transducer $T_R$, and may make a determination reflective of the condition of the bone, and provides an output.

An Integral Diagnostic Unit

Figure 2:
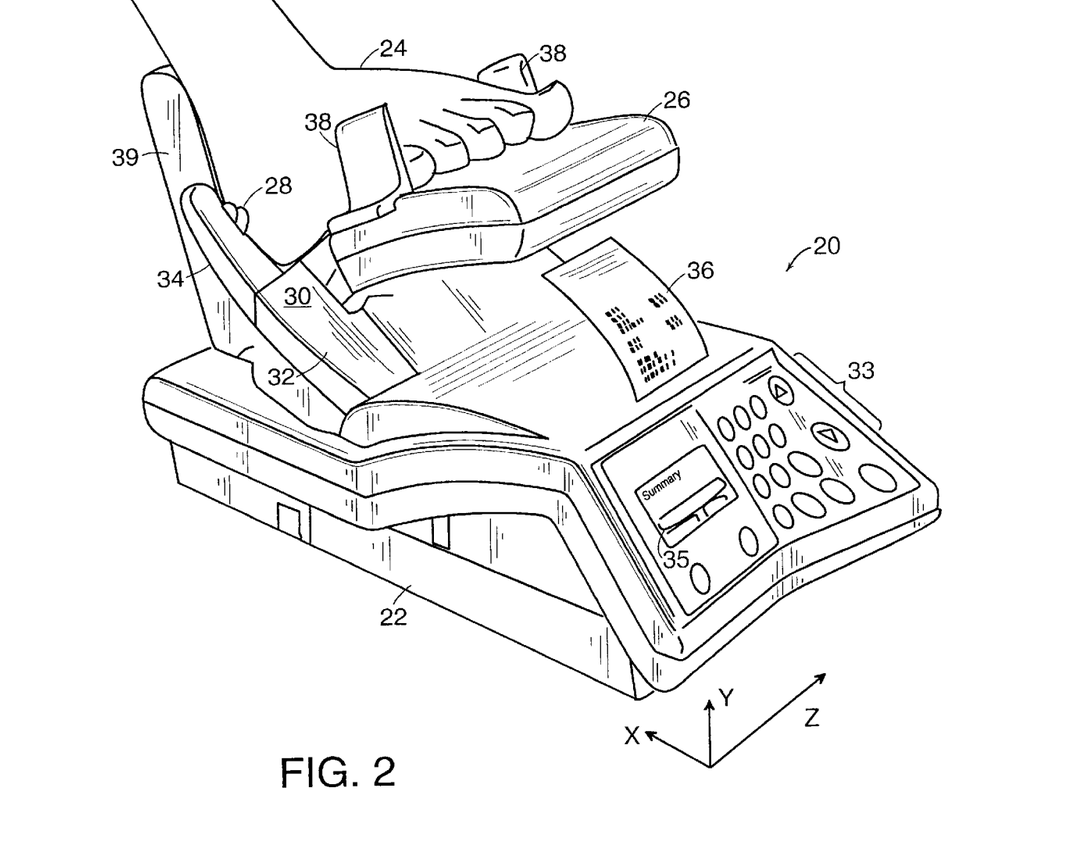
FIG. 2 is a perspective view of an implementation of the system of FIG. 1 in accordance with a preferred embodiment of the invention.

FIG. 2 is a perspective view of an ultrasound bone diagnosis system in accordance with a preferred embodiment of the present invention. Various methods of analyzing the acoustic signals obtained through use of the described system for deriving clinically useful measures are known in the art. Embodiments of the present invention include hardware applicable to various known analysis methods, and the use of any analysis method is within the scope of the invention as claimed herein. An integral bone ultrasound diagnostic unit is shown in perspective and designated generally by numeral 20. For performing measurements of bone qualities, a base 22 of the diagnostic unit 20 is placed on a convenient surface such as the floor, and a foot 24 of a subject is placed on a platform 26. Under some circumstances, it may be advantageous to vary the angular orientation of platform 26 with respect to base 22, such as for comfortably accommodating a seated or prone subject, in which case variability of the orientation of platform 26 may be provided by any tilting mechanism known in the mechanical arts. An orientation of the platform 26 may thus be specified either at the time of manufacture or, in accordance with an embodiment of the invention, at the time of use of the invention.

In accordance with preferred embodiments of the present invention, the axes of transducers 28 are not constrained to be coaxial or even nearly so, nor is a particular angular relationship to base 22 sought for advantageous operation of the device. Thus the term "spaced relationship," as used herein and in any appended claims in the context of transducer placement with respect to the foot or any other body part, refers to both spatial distance and angle.

The following labeling conventions are adopted for convenience only: the fore-aft axis of the base is referred to as the x axis, the axis perpendicular to the bases is referred to as the y axis, and the third axis, perpendicular to the other two axes, and in a direction roughly between the inside and outside of the foot, is referred to as the z axis.

Transmission of an acoustic signal through the bone of foot 24 is provided by transducer 28 which emits acoustic energy while the energy is received by a corresponding transducer (not shown) on the opposing side of foot 24.

Transducer 28 is discussed in further detail below, however, the use of any acoustic transducers in the manner described for ultrasonic assay of bone are within the scope of the invention. Either of the transducers 28 on opposing sides of foot 24 may be used for transmission of the acoustic signal, while the other may be used for reception of the acoustic signal and conversion of the sound wave to an electrical signal. Transducers 28 may be mounted within a spring-loaded sleeve or otherwise so as to provide a constant force of the transducer against the skin of foot 24.

It is known that the positioning, in the x-y plane, of the transmit and receive transducers may be of significant clinical importance to the processing and interpretation of the measurement data. Aspects of applying the variation with position of information such as various Ultrasound Bone Indices (UBIs) are discussed in a copending U.S. patent application filed Sep. 26, 1997, entitled "Ultrasonic Waveform Assay for Bone Assessment Using Values Mapped over a Region," (Ser. No. 08/938,101), which is herein incorporated by reference.

In accordance with a preferred embodiment of the invention, transducers 28 may be positioned, either manually or through operation of motor drives contained within the apparatus, at specified positions in the x-y plane as follows. Each of the two transducer arms 30 consists of an interior segment 32 and an exterior segment 34. Interior segments 32 of the two transducer arms 30 may pivot jointly about an axis fixed with respect to base 22 of the unit 20. Additionally, exterior segment 34 may be telescoped outward from interior segment 32 thereby increasing the distance between the axis fixed with respect to the base and the respective transducers 28. The distance between the fixed axis and the respective transducers 28 defines a radial coordinate which may be referred to as r. The angle through which transducer arms 30 are rotated with respect to an arbitrary fiducial angle may be referred to as $\theta$. Thus, the description of the position of transducers 28 in radial coordinates $(r,\theta)$ is equivalent to a description in terms of x and y.

Additionally, in accordance with an alternate embodiment of the invention, transducer arms may pivot, in a scissor-like fashion, about a real or virtual pivot so as to allow the spacing between the transducers to vary. Spring loading of the transducer arms may be applied to close the transducers toward one another and about the intervening foot 24 of the subject.

In order for a clinical user to employ the integral apparatus described, an interface is provided between the processor and the user both by inputs and outputs disposed on the base of the measurement unit. On one hand, the input may be, for example, a keypad 32. On the other hand, one or more outputs may include, for example, display 34 and printout 36, either of which may provide data in any form clinically useful to the user.

Reproducible positioning of a foot with respect to the platform and thus with respect to the transducers is a problem addressed by certain embodiments of the invention. Since rigid capture of the foot or the heel is uncomfortable to many patients, an alternative method of defining the position of the foot in a reproducible manner as taught in accordance with embodiments of the present invention is often advantageous. The rearward position of the heel may be defined, in accordance with embodiments of the present invention, by placing the back of the heel against a heel post. The orientation of the foot is uniquely defined if the angles of rotation about the three axes, x, y and z, are all defined. Rotation about y, the axis perpendicular to the platform at the heel post and parallel to the plane of the platform corresponds to moving the toes left or right when the back of the heel is stationary. Rotation about the z axis, the axis running in the direction between the outside and the inside of the foot, corresponds to a rotation moving the toes downward with respect to the platform while the heel moves upward, or vice versa. Rotation about the x axis, the axis running from the back to the front of the platform, corresponds to a motion downward on the outside of the foot and upward on the inside, or vice versa. Such a motion could originate at one or more of the ankle, knee, and hip joints.

In order to define the rotation about the y axis, mechanical devices may be used to define the placement of the foot at two positions, one near the forefoot and one near the heel, which can be conveniently chosen at a location accessible to the transducers.

Similarly, the position of foot 24 at a second fore-aft position on platform 26, where transducers 28 are disposed to either side may also be repeatably defined in accordance with an embodiment of the invention. Transducers 28 are mounted in generally opposed relation to one another however, in accordance with a preferred embodiment of the invention, the coaxiality of the transducers is not sought since other orientations are preferred for good contact with the foot. As discussed below, the transducers behave like point sources over a large spatial angle. Since, as described above, the sections of transducer arms 30 bearing transducers 28 may move outward in a scissor-like motion, the relative displacement in the z direction of the respective transducer arms defines a position of the intervening foot 24. For a fixed translational position in the xy plane, the position of the foot causing an equal displacement of each transducer arm is a uniquely defined position and may serve for reproducible placement of the foot. Therefore, in accordance with an embodiment of the invention, a scale is provided for sighting the lateral displacements of the transducer arms so that the foot may be placed so as to establish an equal displacement of the transducer arm on either side.

In order to define the lateral position of the forefoot on platform 26, two laterally spaced guides 38 are movably disposed at a typical position of the forefoot of the subject. Guides 38 are mechanically constrained, as known in the mechanical arts, so that they may move outward in the z direction against a spring force, but, in so moving, their midpoint remains fixed with respect to platform 26.

The rotation about the z axis can be defined by exercising care that the subject's foot is held flat against the platform, allowing neither the heel nor the toes nor any point between the heel and the toes to rise unnaturally above the platform. Sensing devices such as pressure sensors at a plurality of locations on the platform may be used for this purpose, as apparent to a person of ordinary skill in the art.

Rotation about the x axis is generally small and may transpire as a subject seeks a comfortable position, especially when the subject is seated. As a means for minimizing such rotations (as might result from motions in one or more of the ankle, knee, and hip joints), a supporting structure 39, such, for example, as the "Achilles trap" shown, may be provided to support the back of the leg at the Achilles tendon at a specified orientation with respect to platform 26. Constrained rotation of the foot may advantageously enhance reproducibility of the ultrasound measurements. An "Achilles trap," as used in this description and in the appended claims, refers to a device for repeatably positioning the Achilles tendon of the subject by providing a lateral force on either side of the midline of the tendon to allow the subject to center the leg on the basis of tactile sensation. It is understood that devices that engage or detect the leg at locations other than the Achilles tendon may be used within the scope of the invention to similar effect.

The position of the transducers may be monitored by using potentiometers, shaft encoders, or other suitable sensors disposed in relation to the x and y axes. Transducers 28 are preferably biased inwardly toward each other (by one or more springs or other means) to assure good contact with the heel area of the subject for ultrasound transmission. As another example, magnets and hall effect devices to monitor the location of the transducers, may be mounted on the various moving and stationary components of the apparatus.

Figure 8:
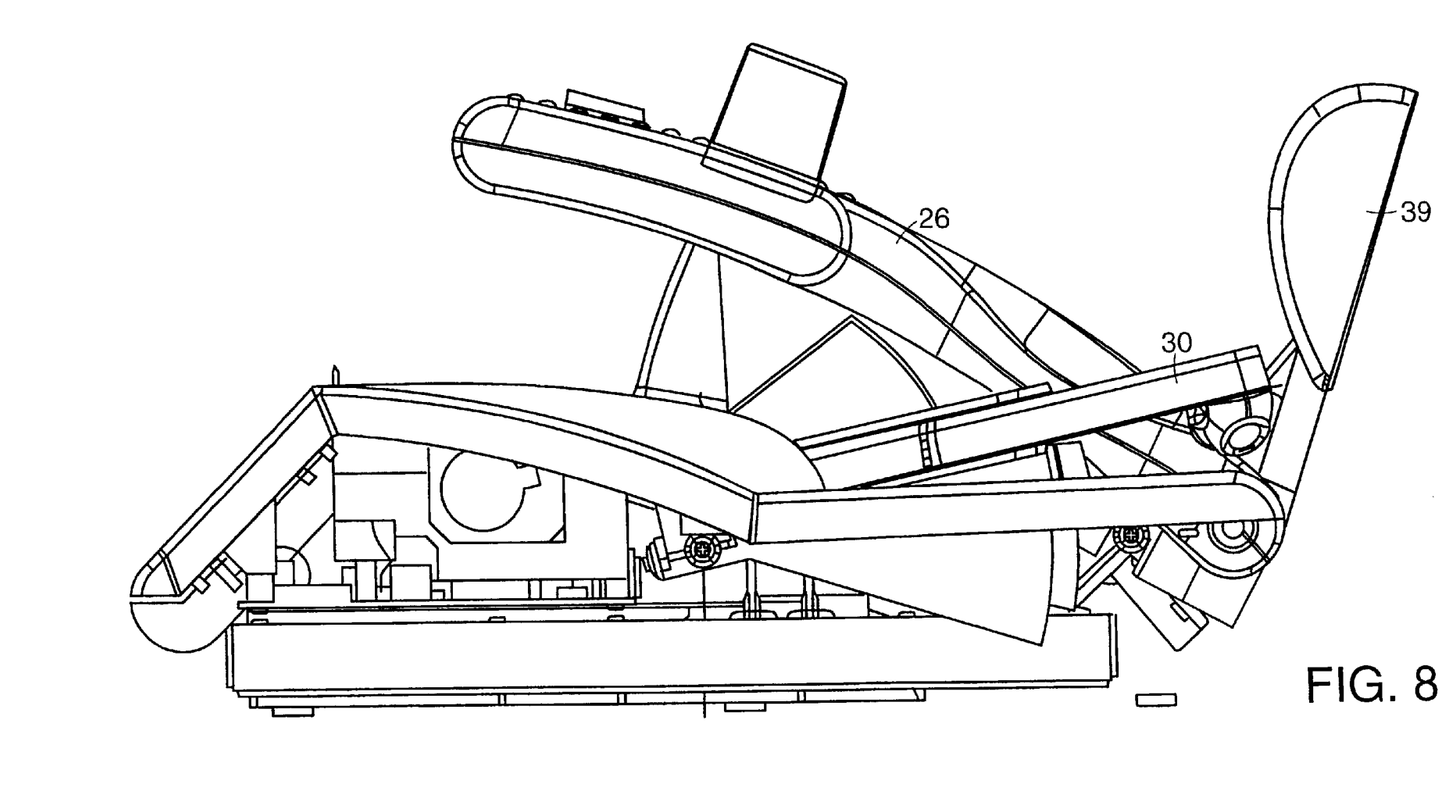
FIG. 8 is a side cutaway view of the apparatus of FIG. 2.
Figure 9:
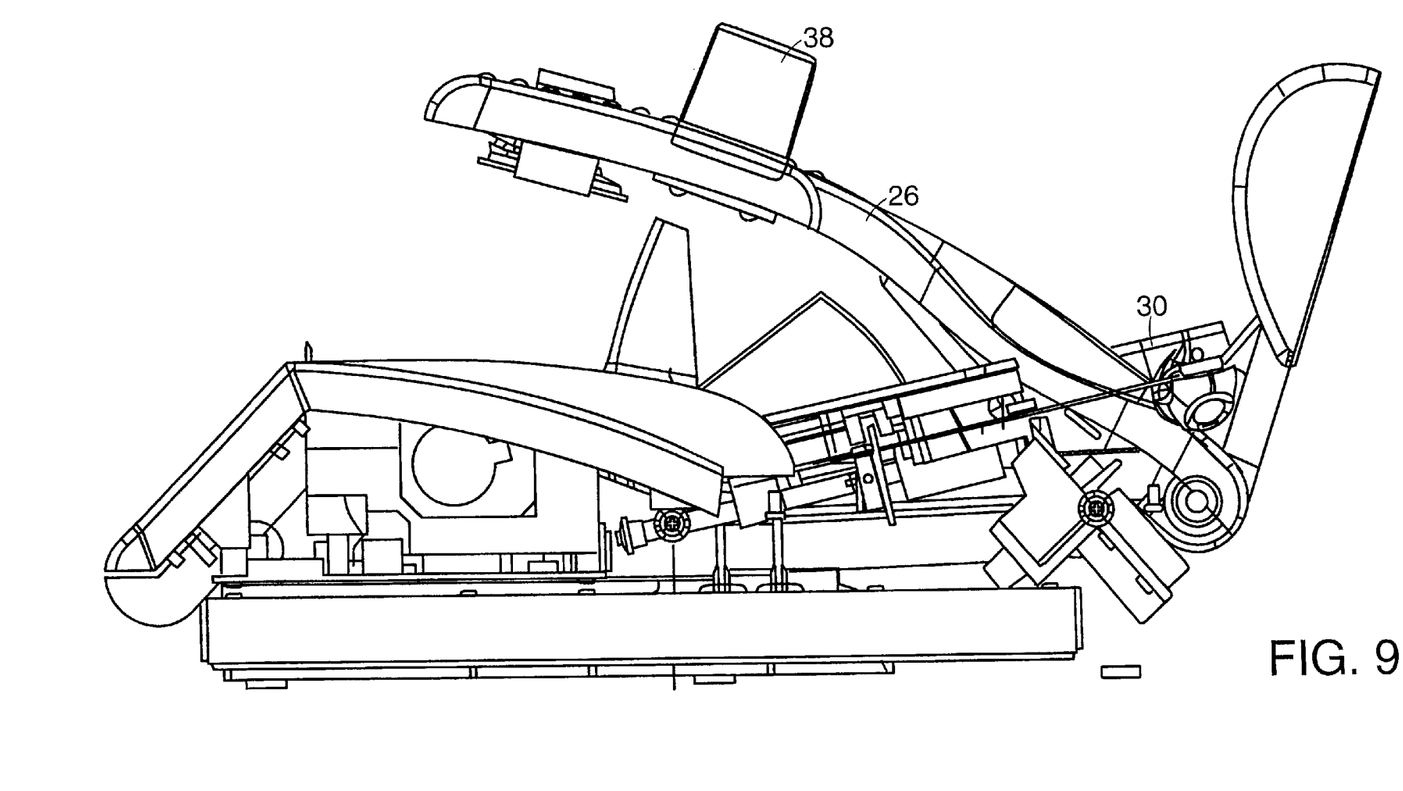
FIG. 9 is a further cutaway view of the apparatus of FIG. 2.

As discussed above in connection with FIG. 8, the yoke may be moved manually or it may be moved under motor control by suitably mounted motors associated with each degree of freedom.

Transducer housing

Measurement procedures, such as those described in the references cited above, take advantage of the fact that healthy bone and osteoporotic bone respond differently to ultrasound inputs. Our investigations have led to the discovery that healthy and osteoporotic bone can be better distinguished by utilizing measures dependent in detail upon the time signature of the whole or part of acoustic pulses transmitted through the bone and not only on global characterizations of propagation through bone such as the broadband ultrasound attenuation (BUA). We have found that the difference in effects, moreover, between healthy and osteoporotic bone is not one that can be measured wholly by looking at the prior art BUA. The procedures outlined in the patents cited above take advantage of these and other observations. Various measures, those referred to as UBIs, have been described in the references cited above and incorporated herein by reference.

It is desirable for all of the UBI measures that the impulse response of both the transmitting and the receiving transducer be of short time duration. This is especially so for those UBI measures that are explicitly based on the transient response of the signal that has passed through the bone. In addition, it is desirable that the transient response be substantially independent of the angle of propagation (i.e., the angle between the transmitting and the receiving transducers) and also substantially independent of the temperature. It is similarly desirable that the coupling from electrical to ultrasonic energy be accomplished with minimal energy loss, and that the coupling of energy from transducer to subject and from subject to transducer exhibit minimal dependence on the specific shape of the subject's foot.

Several design elements in the transducer contribute to achieving a transient response with a desirable combination of these properties. These include the thickness and lateral extent of the active piezoelectric element, as well as the material and geometry of the transducer cap used to hold the active element. These are now described with reference to FIG. 5, which shows a cross section of a transducer unit, designated generally by numeral 50, suitable for use in the apparatus of FIG. 2. Transducer unit 50 utilizes a piezoelectric element 52, which is unusual in that its aspect ratio, is the ratio of its lateral dimension to its axial dimension, is of the order 1.5:1. Such a ratio is usually viewed as undesirable, and more typical aspect ratios are at least 5 or 10:1, so as to avoid complex vibration modes in addition to the desired longitudinal mode radiating in the direction of the subject's foot. In the present case, however, the smaller aspect ratio may advantageously facilitate contact between the transducer and the foot, giving a wide-angle, point-source-like response. Typical dimensions for a piezo element of our design are a diameter of 0.125 inches (0.32 cm) and a thickness of 0.080 inches (0.20 cm). The element is bonded between backing 54 and transducer cap 56. Backing 54 is typically lead, tin-lead, or other metal or insulator as known in the acoustic arts. Details of the contact to the piezoelectric element depend on the backing type and conductivity. Transducer cap 56 is preferably a hard plastic material such as ABS, and is coated with an electrically conducting material such as a sputtered or plated metal or silver paint on the interior. Leads of coaxial cable 58 are connected to backing 54 and the conductive coating of transducer cap 56 which are electrically coupled in turn to the piezoelectric element 52. In cases where an insulating backing is used, electrical contact may be made to the back surface of the piezoelectric element. The back of transducer unit 50 is potted in epoxy or other suitable material.

Figure 5:
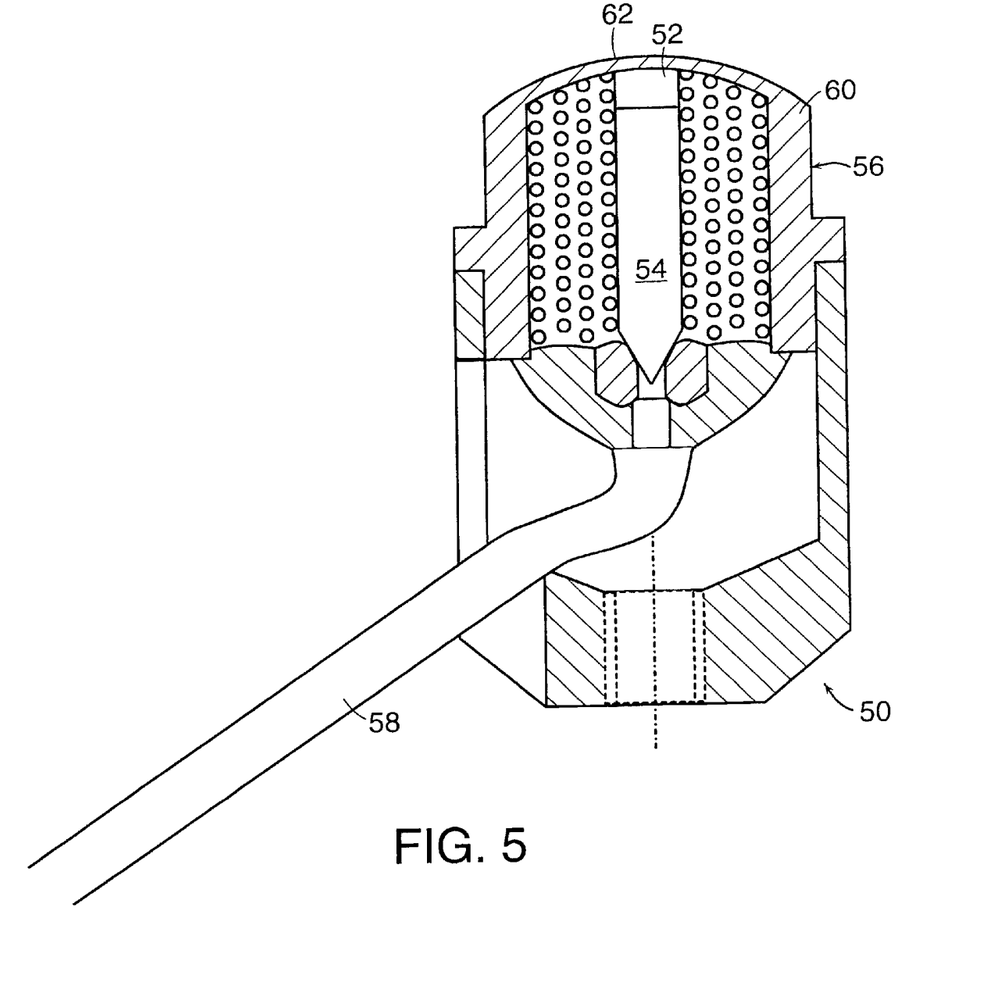
FIG. 5 is a cross-section of a transducer and a transducer housing, in accordance with a preferred embodiment of the invention, suitable for use in the apparatus of FIG. 2.

Transducer cap 56 is comprised of a cylindrical portion coaxial with the piezo crystal and a substantially hemispherical portion which is in intimate contact with the piezo crystal in the forward direction. Acoustically absorbent filler 60 is used to damp ringing. In particular, the forward section 62 of transducer cap 56 is preferentially curved in shape, thus reflecting acoustic energy incident upon it from directions other than the forward direction into the absorbent filler and suppressing the excitation of spurious modes. The shape of forward section 62 of transducer cap 56 may be hemispherical, for example. The curvature of forward section 62 is chosen to help optimize the response of the device as taught below.

Figure 3A:
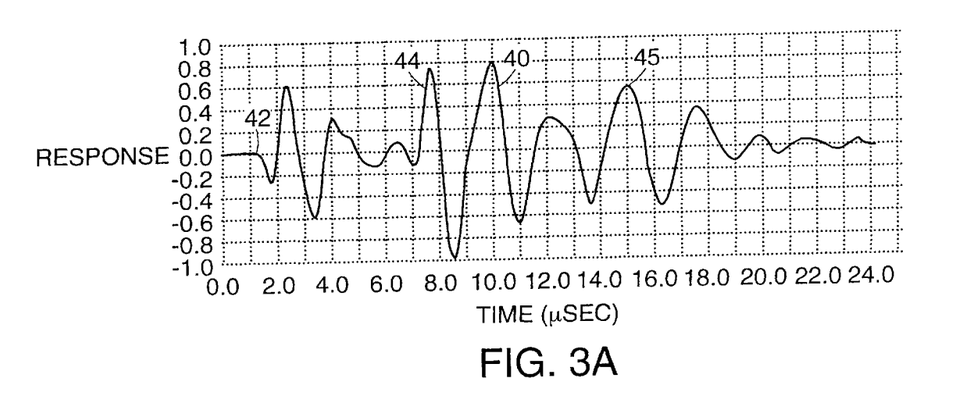
FIG. 3A provides a plot showing the stored output of transducer 13 of FIG. 1 in response to an excitation waveform, generated by the system of FIG. 1 and transmitted through a water bath from an experimental transducer with poor transient response.

The material content, thickness, and shape of the forward section of the transducer cap 56 are important design parameters for optimizing transducer response. This is illustrated by inspecting the response of an experimental device made with a thickness of forward section 62 of 0.375" (about 9.5 mm). Forward section 62, between piezoelectric element 52 and the subject is thicker, in this case, than in a preferred embodiment. FIG. 3A shows a plot of the response of one such experimental transducer transmitting though a water bath to a second identical transducer in coaxial orientation. The electrical drive for this and subsequent figures is a pulse that is short on the time scale of microseconds plotted along the horizontal axis. The time domain response 40 consists of multiple elemental responses. A first response 42 begins at about 1 microsecond on the abscissa of FIG. 3A, while a second response 44 begins about 5.5 $\mu$s later. This 5.5 $\mu$s delay agrees with the difference in propagation time expected between a longitudinal and a shear mode in the front face of transducer cap 56 as used in the experiment depicted. First response 42 would thus correspond to a disturbance that propagates as a longitudinal mode in each transducer. Second response 44 would correspond to a disturbance that propagates as a shear mode in the front face of cap 56 of one transducer and as a longitudinal mode in the second transducer. In this case, the coupling between the water medium employed in the experiment and the transmitting transducer would necessarily involve a mode conversion from a shear to a longitudinal mode, since water does not support a shear acoustic mode. A third response 45 would correspond to a disturbance that propagates as a shear mode in plastic cap 56 of both transducers and that undergoes mode conversion between shear and longitudinal modes at each interface between the caps 56 and the water medium.

Figure 3B:
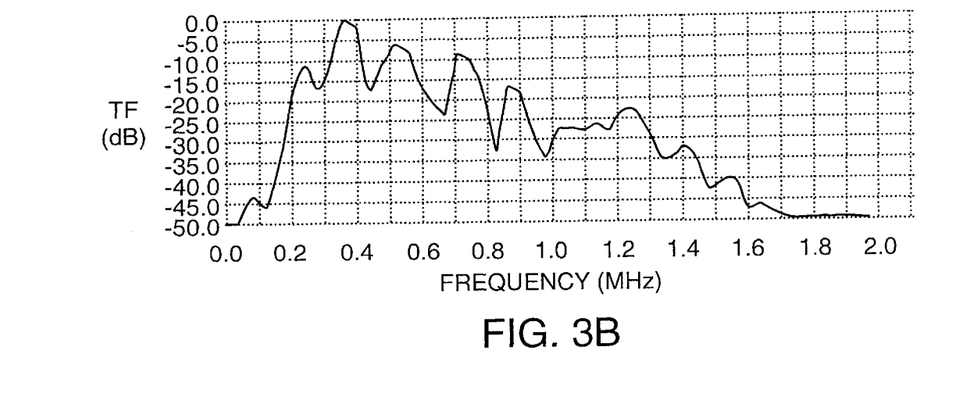
FIG. 3B provides a plot of the spectral content associated with the plot of FIG. 3A.

The response shown in FIG. 3A is undesirable because the time signature is of long duration. The spectral content of the received pulse, as depicted in FIG. 3B, additionally shows large variations over intervals of about 100 kHz. A frequency response with small variations over such frequency intervals is preferable for measures of bone density that are derived from frequency response. Conventional BUA measures are examples of such measures that require small response variations with frequency.

Figure 4A:
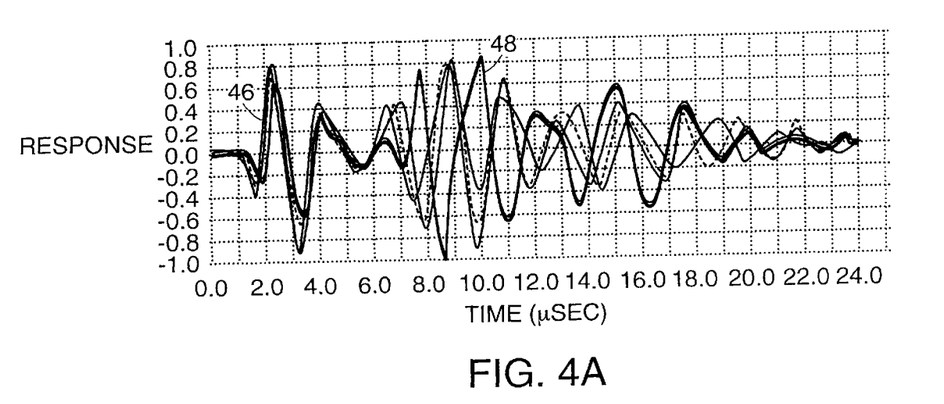
FIG. 4A provides a series of plots showing the output of transducer 13 of FIG. 1 in response to an excitation waveform, generated by the system of FIG. 1 and transmitted through a water bath from the experimental transducer of FIGS. 3A and 3B at a variety of angles showing the ringing and angular sensitivity characteristic of suboptimal transducers.
Figure 4B:
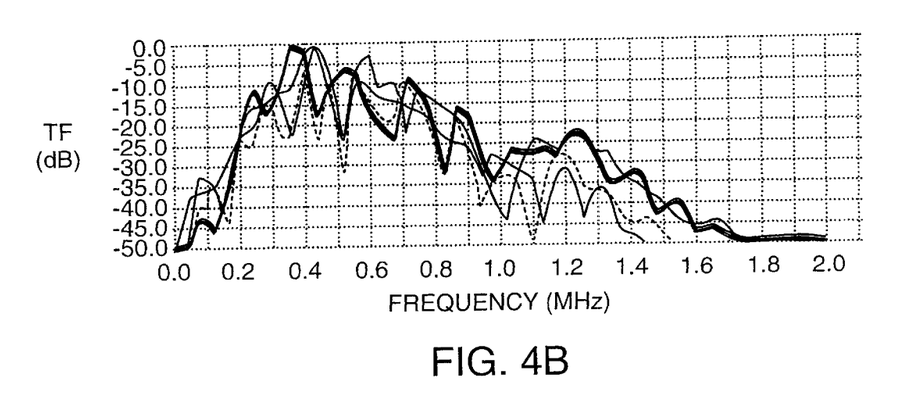
FIG. 4B provides a plot of the spectral content associated with the plots of FIG. 4A.

Further problematic features of the experimental transducer response of FIGS. 3A–3B is described with reference to FIGS. 4A and 4B. FIG. 4A shows the temporal response of the transducer pair of FIGS. 3A–3B for relative orientations of the transducers ranging from coaxial to relative orientations of the longitudinal axes of the transducers of 10°, 20°, 30°, 40° and 50°. FIG. 4B shows the spectral response of the same device pair for the identical set of relative orientations of the longitudinal axes of the transducers. First response 46 is relatively independent of the angle between the longitudinal axis of the transducer and the emission field, however later responses 48 vary greatly with angle. The variation with angle is likely explained by the slightly different propagation times to the curved front face and to variations with angle of the coupling between shear modes in the plastic cap and longitudinal modes in water, as described above. It is well known that such coupling is sensitive to boundary conditions, and thus to propagation angle and to the curvature of the front face.

It thus appears that transducer response is determined in part by multiple propagation modes in the transducer cap. The material and geometry of the cap combine to determine the extent to which multiple modes are excited and the manner in which such modes combine to give the net device response.

Design of the transducer cap, in accordance with preferred embodiments of the invention entails optimization of material and geometry so as to provide one or more of the following design objectives:

a. short transient response;

b. efficient transduction between electrical excitation and acoustic energy propagated in the subject;

c. substantial independence of output with respect to emission (or reception) angle and temperature;

d. repeatable acoustic coupling between the transducer and a body part under conditions of varying geometries of the body part; and e. substantial independence of acoustic measurements on variations in the geometry of the measured body part.

An optimal thickness of the forward section 62 is found to be approximately 30 mils, in ABS plastic, in order to provide relatively high throughput of acoustic energy, minimal dependence of the output on angle, and minimal variations of response with temperature. IN accordance with a preferred embodiment of the invention, the front face 62 has a radius of curvature of 5/16", which allows favorable coupling to the foot and also contributes to a desired transient response.

Figure 6A:
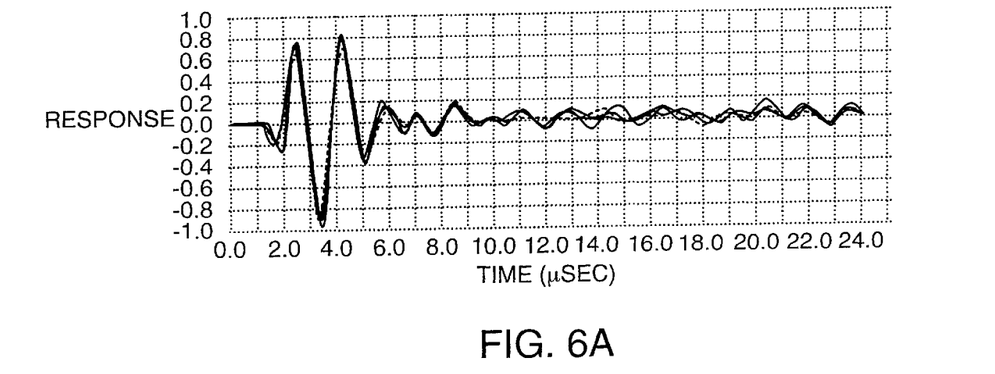
FIG. 6A provides a series of plots showing the output of a transducer such as that of FIG. 5 in response to an excitation waveform, as transmitted by a transducer through a water bath at a variety of angles in accordance with an embodiment of the invention, showing insensitivity to angle.
Figure 6B:
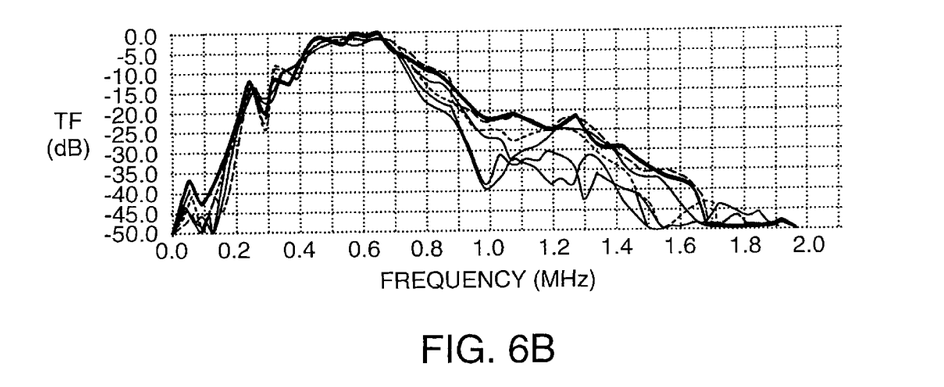
FIG. 6B provides a series of plots of the spectral content associated with the plots of FIG. 6A.
Figure 7:
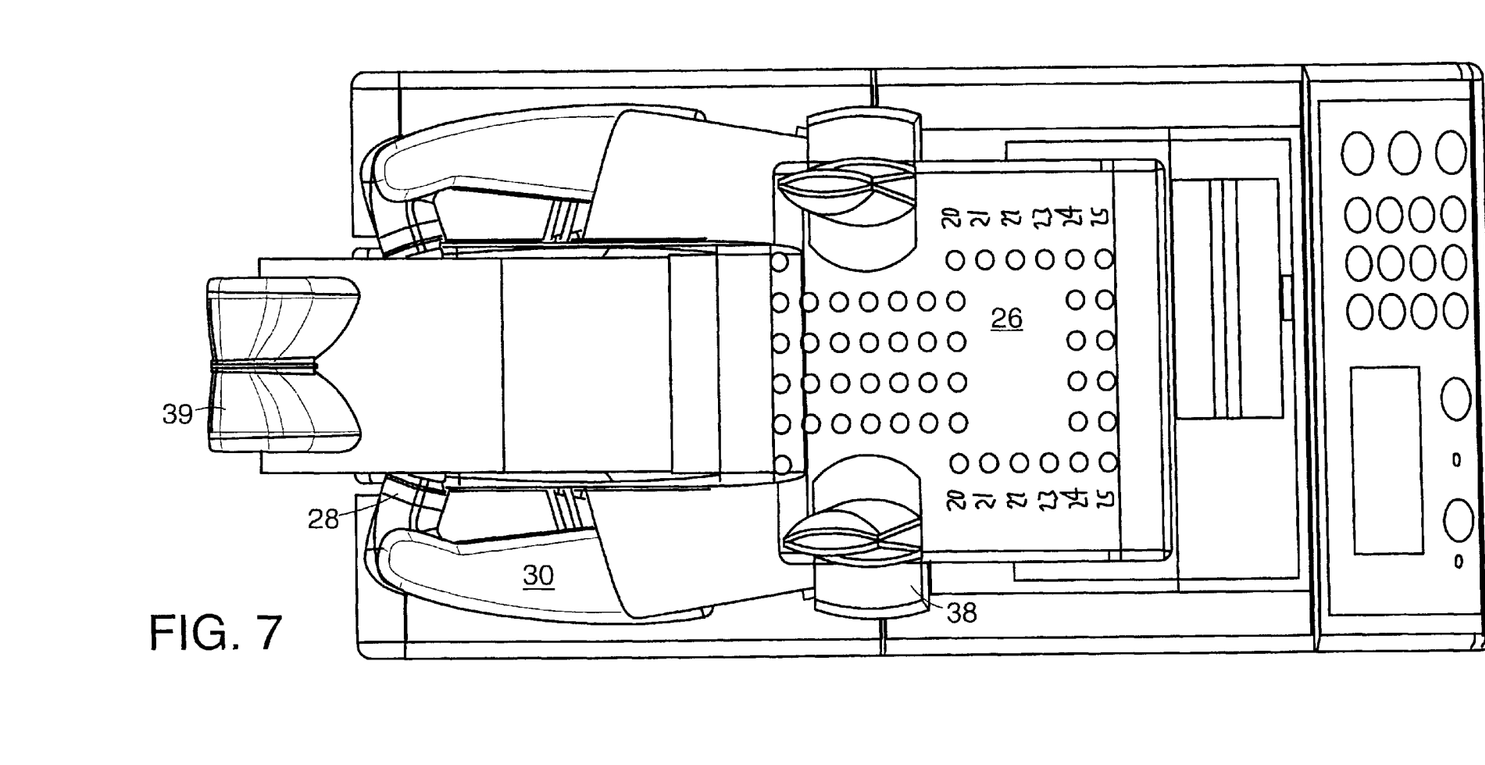
FIG. 7 is a top view of the apparatus of FIG. 2.

Referring to FIGS. 6A, the temporal response to an impulse is shown for a transducer unit in accordance with an embodiment of the invention. The response is seen to be damped after approximately 6 $\mu$s is at all angles, and the early pulse appears nearly identical at angles up to 50°. The spectral response of FIG. 6B is similarly seen to be substantially independent of angle over the aforesaid range of angles. The differences in response at different angles are mostly concentrated at higher frequencies as expected from diffraction theory. Because the energy is lower at these higher frequencies, and because of the strong low-pass filtering action of bone, these residual differences at high frequency have a minimal effect on acoustic measurements of bone. Thus, it is evident that the transducers behave as point sources especially with respect to the shape of the transient response of the system.

It should be noted that the described embodiments of the invention may be used in combination of two or more of the above embodiments for characterization of properties of bone. The described embodiments of the invention are intended to be merely exemplary and numerous variations and modifications will be apparent to those skilled in the art. All such variations and modifications are intended to be within the scope of the present invention as defined in the appended claims.

What is claimed is:

1. An apparatus for performing a measurement with respect to a foot of a vertebrate subject, the measurement characterizing the behavior of an acoustic wave in a bone disposed within the foot, the apparatus comprising:

a. a base having a spatial orientation fixed for a duration of the measurement;

b. a platform for receiving the foot of the subject, the platform being coupled to the base at a specified angle with respect to the base;

c. a foot orientation mechanism for reproducible placement of the foot of the subject on the platform;

d. a first transducer arm for supporting a first acoustic transducer in spaced relationship with respect to the foot of the subject;

e. a second transducer arm for supporting a second acoustic transducer in spaced relationship with respect to the foot of the subject;

f. a member for mounting the first and second transducer arms in moveable relationship to the base so as to permit coupled two-dimensional motion of the first and second transducers over regions of the foot including the calcaneus;

g. a waveform generator for causing the first transducer to produce an acoustic waveform that is propagated into the subject and received by the second transducer along a path that includes the bone; and     h. a processor for determining a characteristic of the behavior of the waveform along the path and providing an output;

wherein the waveform generator, the platform, the transducer arms, and the processor are contained in an integral assembly.

2. An apparatus according to claim 1, wherein the foot orientation mechanism includes a forefoot centering arrangement.

3. An apparatus according to claim 2, wherein the forefoot centering arrangement includes a pair of laterally disposed guides for laterally defining the edges of the foot, the guides being mechanically constrained such that the midpoint between the guides remains fixed regardless of the distance between them.

4. An apparatus according to claim 1, further including a display for displaying the output of the processor, the display being contained in the integral assembly.

5. An apparatus according to claim 1, further including a measuring arrangement for determining the relative displacement of each of the first and second transducer arms for permitting reproducible placement of the foot on the platform.

6. An apparatus according to claim 1, wherein the foot orientation mechanism includes sensors for detecting placement of the foot relative to a centerline of the platform.

7. An apparatus according to claim 1, further including sensors disposed at a plurality of specified locations on the platform for ensuring that the foot is held flat against the platform.

8. An apparatus according to claim 1, wherein the platform includes a heel post for defining the rearward extent of placement of the heel on the platform.

9. An apparatus according to claim 1, further comprising a calf positioning mechanism for supporting the calf of the subject at a specified orientation with respect to the platform of the apparatus.

10. An apparatus according to claim 8, wherein the calf positioning mechanism includes an Achilles trap.

11. An apparatus according to claim 1, further including a transducer positioning mechanism for varying the spaced relationship of the first and second transducers with the foot of the subject.

12. An apparatus according to claim 1, wherein the first and second transducer arms are extensible for permitting the distance between the first transducer and the mounting member and the distance between the second transducer and the mounting member to be varied commensurately.

13. An apparatus according to claim 1, wherein the first and second transducer arms are coupled to a pivot fixed with respect to the base for permitting motion of each transducer arm in parallel in a direction perpendicular to lines between the pivot and each of the first and second transducers.

14. A transducer unit for emitting an acoustic wave, the transducer unit having an output substantially independent of emission angle for emission angles less than approximately 30° from a forward direction, the transducer unit comprising:
   a. a piezo-electric element having a lateral dimension and an axial dimension for generating the acoustic wave;
   b. a transducer cap having a wall with an interior surface surrounding the piezo-electric element circumferentially and in the forward direction and intimately coupled to the piezo-electric element in a contact region in no more than the forward direction;
   c. a backing for absorbing acoustic energy radiated by the piezo-electric element in a posterior direction; and
   d. a damping filler for filling a volume lying between the piezo-electric element and a circumferential portion of the transducer cap.

15. A transducer unit according to claim 14, wherein the inner surface of the wall of the transducer cap outside the contact region is angled in such a manner as to reflect acoustic energy impinging upon it away from the piezo-electric element.

16. A transducer unit according to claim 14, wherein the lateral dimension of the piezo-electric element is less than twice the axial dimension of the piezo-electric element.

17. A transducer unit according to claim 14, wherein the transducer cap extends beyond the piezo-electric element in the forward direction for a distance selected so as to minimize variation of acoustic output of the unit with respect to temperature and angle of emission.

18. A transducer unit according to claim 14, wherein the transducer cap includes plastic.

19. A transducer unit according to claim 14, wherein a forward portion of the wall of the transducer cap is curved such as to favorably combine contributions of longitudinal and shear modes of acoustic energy to acoustic energy propagation in the subject.

20. A transducer unit according to claim 14, wherein a forward portion of the wall of the transducer cap is of hemispherical section such as to favorably combine contributions of longitudinal and shear modes of acoustic energy to acoustic energy propagation in the subject.

21. A transducer unit according to claim 14, wherein the damping filler includes polyurethane.

22. A transducer unit for receiving an acoustic wave, the transducer unit having an output substantially independent of detection angle for detection angles less than approximately 30° from a forward direction, the transducer unit comprising:
   a. a piezo-electric element having a lateral dimension and an axial dimension for generating the acoustic wave;
   b. a transducer cap having a wall with an interior surface surrounding the piezo-electric element circumferentially and in the forward direction and intimately coupled to the piezo-electric element in a contact region in no more than the forward direction;
   c. a backing for absorbing acoustic energy radiated by the piezo-electric element in a posterior direction; and
   d. a damping filler for filling a volume lying between the piezo-electric element and a circumferential portion of the transducer cap.

23. An apparatus for performing a measurement with respect to a body part, the measurement characterizing the behavior of an acoustic wave within the body part, the apparatus comprising:
   a. a base having a spatial orientation fixed for a duration of the measurement;
   b. a first transducer arm for supporting a first acoustic transducer in spaced relationship with respect to the body part;
   c. a second transducer arm for supporting a second acoustic transducer in spaced relationship with respect to the body part;
   d. a member for mounting the first and second transducer arms in moveable relationship to the base so as to permit coupled two-dimensional motion of the first and second transducers over regions of the body part;
   e. a waveform generator for causing the first transducer to produce an acoustic waveform that is propagated into the body part and received by the second transducer; and
   f. a processor for determining a characteristic of the behavior of the waveform along the path and providing an output;
wherein the first and second transducer arms are extensible for permitting the distance between the first transducer and the mounting member and the distance between the second transducer and the mounting member to be varied commensurately and wherein the first and second transducer arms are coupled to a pivot fixed with respect to the base for permitting motion of each transducer arm in parallel in a direction perpendicular to lines between the pivot and each of the first and second transducers.

24. A method for characterizing the behavior of an acoustic wave in a bone disposed within a foot of a vertebrate subject, the method comprising:
   a. providing an apparatus having:
      i. a platform for receiving the foot of the subject;
      ii. a first transducer arm for supporting a first acoustic transducer in spaced relationship with respect to the foot of the subject;
      iii. a second transducer arm for supporting a second acoustic transducer in spaced relationship with respect to the foot of the subject;
      iv. a member for mounting the first and second transducer arms in moveable relationship to the base so as to permit coupled two-dimensional motion of the first and second transducers over regions of the foot including the calcaneus; and v. a processor for determining a characteristic of the behavior of the waveform along the path;

wherein the waveform generator, the platform, the transducer arms, and the processor are contained in an integral assembly;

b. orienting the foot of the subject in a specified and reproducible orientation with respect to the platform;

c. exciting an acoustic wave for propagation into the subject with the first transducer;

d. receiving the acoustic wave with the second transducer; and e. calculating a characteristic of the waveform along the path.

25. A method according to claim 24, further including the step of displaying at least one output of the processor.

* * * * *